United States Patent
Lee

(10) Patent No.: US 9,216,007 B2
(45) Date of Patent: Dec. 22, 2015

(54) SETTING A SAGITTAL VIEW IN AN ULTRASOUND SYSTEM

(75) Inventor: Kwang Hee Lee, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 411 days.

(21) Appl. No.: 12/763,008

(22) Filed: Apr. 19, 2010

(65) Prior Publication Data

US 2011/0028841 A1 Feb. 3, 2011

(30) Foreign Application Priority Data

Jul. 30, 2009 (KR) ........................ 10-2009-0069867

(51) Int. Cl.
*A61B 8/00* (2006.01)
*A61B 8/08* (2006.01)

(52) U.S. Cl.
CPC ............... *A61B 8/0858* (2013.01); *A61B 8/467* (2013.01); *A61B 8/483* (2013.01); *A61B 8/523* (2013.01); *A61B 8/469* (2013.01)

(58) Field of Classification Search
USPC ........................................................ 600/443
See application file for complete search history.

(56) References Cited

U.S. PATENT DOCUMENTS

| | | | |
|---|---|---|---|
| 6,102,861 A | 8/2000 | Avila et al. | |
| 7,604,597 B2 | 10/2009 | Murashita et al. | |
| 8,012,090 B2 | 9/2011 | Steen | |
| 8,083,678 B2 | 12/2011 | Abuhamad | |
| 8,216,144 B2 | 7/2012 | Murashita et al. | |
| 2007/0038106 A1* | 2/2007 | Kim et al. | 600/443 |
| 2007/0081705 A1 | 4/2007 | Carneiro et al. | |
| 2007/0249935 A1 | 10/2007 | Deschinger et al. | |
| 2007/0255139 A1 | 11/2007 | Deschinger et al. | |
| 2008/0051653 A1 | 2/2008 | Choi et al. | |
| 2009/0074280 A1 | 3/2009 | Lu et al. | |
| 2009/0082675 A1 | 3/2009 | Gunji et al. | |
| 2009/0227869 A1 | 9/2009 | Choi | |
| 2011/0028842 A1 | 2/2011 | Lee et al. | |

FOREIGN PATENT DOCUMENTS

| | | |
|---|---|---|
| EP | 1 470 784 A2 | 10/2004 |
| EP | 1 923 839 A1 | 5/2008 |

(Continued)

OTHER PUBLICATIONS

"Lee et al.," "Automatic Ultrasonic Measurement of Fetal Nuchal Translucency Using Dynamic Programming," J.F. Martinez-Tinidad et al. (Eds.): CIARP Springer-Verlag Berlin pp. 187-167, 2006.*
Extended European Search Report issued in European Patent Application No. 10159227.7-1265, dated Dec. 17, 2010.
Andrew D. Hull et al., "Detection of Jarcho-Levin syndrome at 12 weeks' gestation by nuchal translucency screening and three-dimensional ultrasound," Prenatal Diagnosis, vol. 12, 2001, pp. 390-394, XP-002312156.

(Continued)

*Primary Examiner* — Tse Chen
*Assistant Examiner* — Patricia Park
(74) *Attorney, Agent, or Firm* — McDermott Will & Emery LLP

(57) ABSTRACT

Embodiments for providing a plurality of slice images are disclosed. In one embodiment, by way of non-limiting example, an ultrasound system comprises: an ultrasound data acquisition unit configured to transmit and receive ultrasound signals to and from a target object to thereby output ultrasound data; and a processing unit configured to form volume data based on the ultrasound data, set a reference slice, a reference point and a window on the volume data based on input information of a user and set a sagittal view for measuring a thickness of a nuchal translucency (NT) of a fetus on the volume data.

5 Claims, 6 Drawing Sheets

(56) References Cited

FOREIGN PATENT DOCUMENTS

| | | | | |
|---|---|---|---|---|
| JP | 05-346963 | | 12/1993 | |
| JP | 2001-513648 | | 9/2001 | |
| JP | EP 1 470 784 | * | 10/2004 | ............... A61B 8/00 |
| JP | 2004-313651 A | | 11/2004 | |
| JP | 2005-102945 A | | 4/2005 | |
| JP | 2006-006932 A | | 1/2006 | |
| JP | 2006-523510 A | | 10/2006 | |
| JP | 2007-289685 A | | 11/2007 | |
| JP | 2007-296330 A | | 11/2007 | |
| JP | 2008-049158 A | | 3/2008 | |
| JP | EP 1 923 839 | * | 5/2008 | ............... G06T 17/00 |
| JP | 2008-142519 A | | 6/2008 | |
| JP | 2008-534082 A | | 8/2008 | |
| JP | 2008-200097 A | | 9/2008 | |
| JP | 2008-284263 A | | 11/2008 | |
| JP | 2009-77961 | | 4/2009 | |
| JP | 2009-207899 A | | 9/2009 | |
| JP | 2011-031022 A | | 2/2011 | |
| KR | 2002-0041290 | | 6/2002 | |
| KR | 10-2008-0004775 | | 1/2008 | |
| KR | EP 1 892 671 | * | 2/2008 | ................ G06T 7/60 |
| WO | WO 98/39474 | | 9/1998 | |
| WO | WO 00/58754 | | 10/2000 | |
| WO | WO 02/43008 | * | 5/2002 | ............. G06T 15/00 |
| WO | WO 02/43008 A1 | | 5/2002 | |
| WO | WO2009/136332 | * | 11/2009 | ............... A61B 8/08 |

OTHER PUBLICATIONS

A.S. Lev-Toaff et al., "Three-dimensional multiplanar ultrasound for fetal gender assignment: value of the mid-sagittal plane," Ultrasound Obstet Gynecol, vol. 16, pp. 345-350, XP-00261257.

Hui-Xiong Xu et al., "Comparison of Two-Dimesional and Three-Dimensional Sonography in Evaluating Fetal Malformations," Journal of Clinical Ultrasound, vol. 30, No. 9, 2002 pp. 515-525, XP-002612158.

Yu-Bu Lee et al., "Automated Ultrasound Measurement of Fetal Nuchal Translucency Using Dynamic Programming," Progress in Pattern Recognition, Image Analysis and Applications Lecture Notes in Computer Science; LNCS, Springer, Berlin, DE, pp. 157-167, XP019045806.

Korean Office Action issued in Korean Patent Application No. 10-2009-0069867, mailed Jul. 7, 2011.

Japanese Office Action issued in Japanese Application No. 2010-108320 dated Oct. 28, 2014, with English Translation.

Japanese Office Action issued in Japanese Application No. 2010-108320 dated Feb. 18, 2014, with English Translation.

Seiji Wada et al, "A prenatal diagnostic test using ultrasound—Consideration on Nuchal translucency" Obstetrical and Gynecological, vol. 73, No. 7, 2006, pp. 881-888.

Seiji Wada et al., "Nuchal translucency," Obstetrical and Gynecological Practice, vol. 58, No. 6, Jun. 2009, pp. 929-933.

* cited by examiner

SETTING A SAGITTAL VIEW IN AN ULTRASOUND SYSTEM

CROSS-REFERENCE TO RELATED APPLICATIONS

The present application claims priority from Korean Patent Application No. 10-2009-0069867 filed on Jul. 30, 2009, the entire subject matter of which is incorporated herein by reference.

TECHNICAL FIELD

The present disclosure generally relates to ultrasound systems, and more particularly to setting a sagittal view for measuring a thickness of a nuchal translucency (NT) of a fetus in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional diagnostic images of internal features of an object (e.g., human organs).

The ultrasound system transmits and receives ultrasound signals to and from a target object (e.g., a fetus) to thereby form a 2D (two-dimensional) ultrasound image of the fetus. Also, when a user sets a sagittal view for measuring a thickness of a nuchal translucency (NT) of the fetus based on the 2D ultrasound image, the ultrasound system may check a chromosomal abnormality of the fetus by measuring the thickness of the NT based on the sagittal view. However, it may be difficult to precisely set the sagittal view on volume data. Thus, there is a problem in that the thickness of the NT may not be measured exactly.

SUMMARY

Embodiments for providing a plurality of slice images in an ultrasound system are disclosed herein. In one embodiment, by way of non-limiting example, an ultrasound system comprises: an ultrasound data acquisition unit configured to transmit and receive ultrasound signals to and from a target object to thereby output ultrasound data; and a processing unit configured to form volume data based on the ultrasound data, the processing unit being configured to set a reference slice, a reference point and a window on the volume data based on input information of a user, and the processing unit being further configured to set a sagittal view for measuring a thickness of a nuchal translucency (NT) of a fetus on the volume data.

In another embodiment, there is provided a method of setting a sagittal view, comprising: a) transmitting and receiving ultrasound signals to and from a target object to thereby output ultrasound data; b) forming volume data based on the ultrasound data; c) setting a reference slice, a reference point and a window on the volume data based on input information of a user; and d) setting a sagittal view for measuring a thickness of a nuchal translucency (NT) of a fetus on the volume data based on the reference slice, the reference point and the window.

In yet another embodiment, there is provided a computer readable medium comprising computer executable instructions configured to perform the following acts: a) transmitting and receiving ultrasound signals to and from a target object to thereby output ultrasound data; b) forming volume data based on the ultrasound data; c) setting a reference slice, a reference point and a window on the volume data based on input information of a user; and d) setting a sagittal view for measuring a thickness of a nuchal translucency (NT) of a fetus on the volume data based on the reference slice, the reference point and the window.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
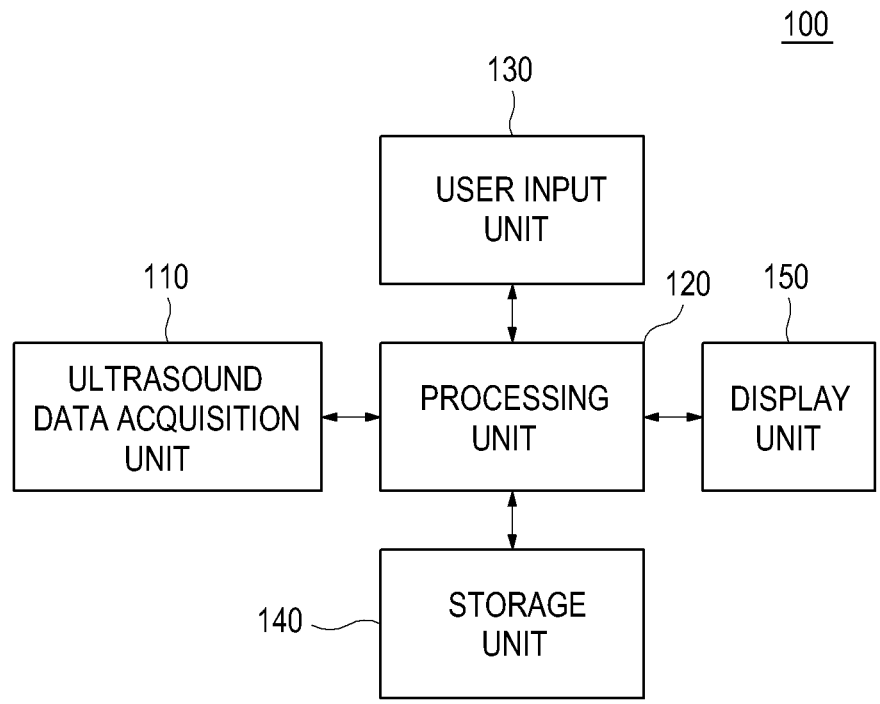
FIG. 1 is a block diagram showing an illustrative embodiment of an ultrasound system.

Referring to FIG. 1, an ultrasound system 100 in accordance with an illustrative embodiment is shown. As depicted therein, the ultrasound system 100 may include an ultrasound data acquisition unit 110. The ultrasound data acquisition unit 110 may be operable to transmit and receive ultrasound signals to and from a target object (e.g., a fetus) to thereby output ultrasound data. The ultrasound data acquisition unit 110 may include a transmit (Tx) signal generating section 111, as shown in FIG. 2.

Figure 2:
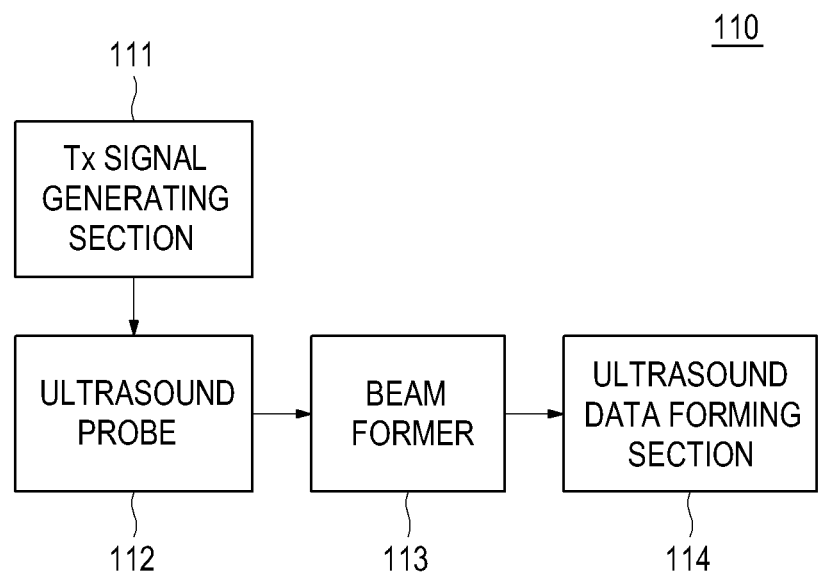
FIG. 2 is a block diagram showing an illustrative embodiment of an ultrasound data acquisition unit.

FIG. 2 is a block diagram showing an illustrative embodiment of the ultrasound data acquisition unit 110. Referring to FIG. 2, the Tx signal generating section 111 may be operable to generate Tx signals. The Tx signal generating section 111 may generate the Tx signals at every predetermined time to thereby form a plurality of Tx signals for obtaining each of frames $F_i$ ($1 \leq i \leq N$) representing the target object, as shown in FIG. 3.

Figure 3:
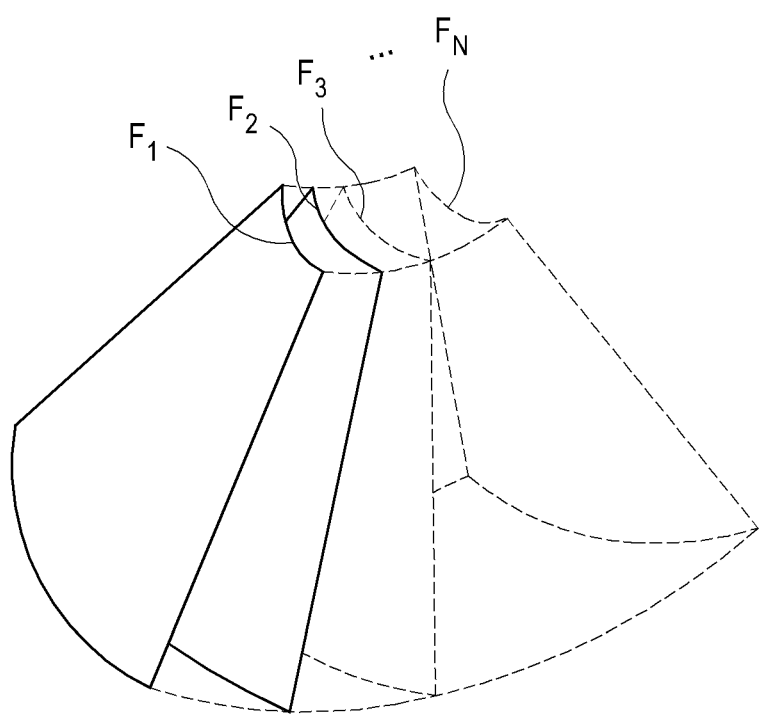
FIG. 3 is a schematic diagram showing an example of acquiring ultrasound data corresponding to a plurality of frames.

FIG. 3 is a schematic diagram showing an example of acquiring ultrasound data corresponding to a plurality of frames $F_i$ ($1 \leq i \leq N$). The plurality of frames $F_i$ ($1 \leq i \leq N$) may represent sectional planes of the target object (not shown).

Referring back to FIG. 2, the ultrasound data acquisition unit 110 may further include an ultrasound probe 112 containing a plurality of elements for reciprocally converting between ultrasound signals and electrical signals. The ultrasound probe 112 may be operable to transmit ultrasound signals into the target object in response to the Tx signals. The ultrasound probe 112 may further receive echo signals reflected from the target object to thereby output received signals. The received signals may be analog signals. The ultrasound probe 112 may include a three-dimensional mechanical probe, a two-dimensional array probe or the like. However, the ultrasound probe 112 may not be limited thereto.

The ultrasound data acquisition unit 110 may further include a beam former 113. The beam former 113 may be operable to convert the received signals into digital signals. The beam former 113 may further apply delays to the digital signals in consideration of distances between the elements and focal points to thereby output digital receive-focused signals.

The ultrasound data acquisition unit 110 may further include an ultrasound data forming section 114. The ultrasound data forming section 114 may be operable to form ultrasound data corresponding to each of the frames $F_i$ ($1 \le i \le N$) based on the digital receive-focused signals. The ultrasound data forming unit 114 may be further operable to perform various signal processing (e.g., gain adjustment) to the digital receive-focused signals.

Figure 4:
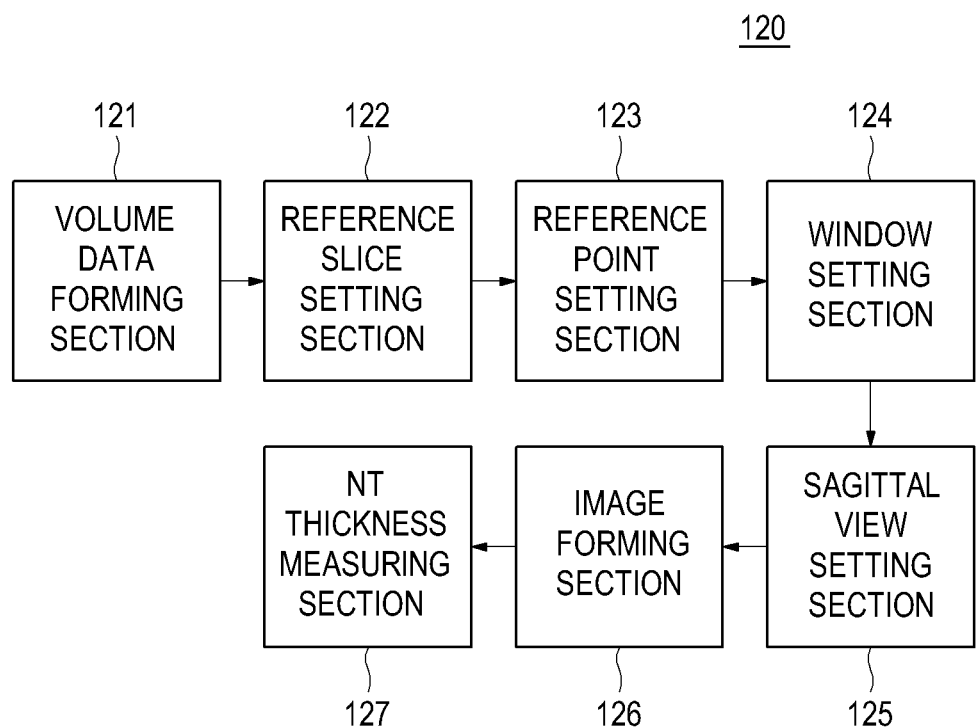
FIG. 4 is a block diagram showing an illustrative embodiment of a processing unit.

Referring back to FIG. 1, the ultrasound system 100 may further include a processing unit 120, which may be coupled to the ultrasound data acquisition unit 110. FIG. 4 is a block diagram showing an illustrative embodiment of the processing unit 120. Referring to FIG. 4, the processing unit 120 may include a volume data forming section 121, a reference slice setting section 122, a reference point setting section 123, a window setting section 124, a sagittal view setting section 125, an image forming section 126 and a nuchal translucency (NT) thickness measuring section 127.

Figure 5:
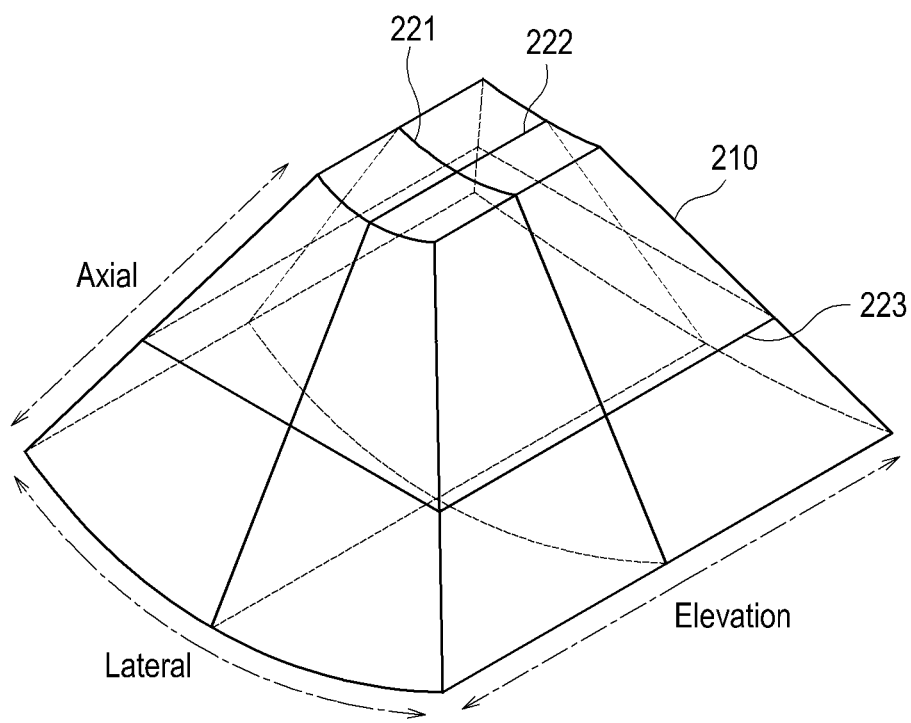
FIG. 5 is a schematic diagram showing an example of volume data.

The volume data forming section 121 may synthesize the ultrasound data corresponding to the frames $F_i$ ($1 \le i \le N$) to thereby form volume data including the frames $F_i$ ($1 \le i \le N$), as shown in FIG. 5. FIG. 5 is a schematic diagram showing an example of volume data 210. The volume data 210 may include a plurality of voxels having brightness values. In FIG. 5, reference numerals 221 to 223 represent an A plane, a B plane and a C plane. The A plane 221, the B plane 222 and the C plane 223 may be mutually orthogonal. Also, in FIG. 5, the axial direction may be a Tx direction of the ultrasound signals, the lateral direction may be a longitudinal direction of the transducer and the elevation direction may be a swing direction of the transducer, i.e., a depth direction of a 3D (three-dimensional) ultrasound image.

Figure 6:
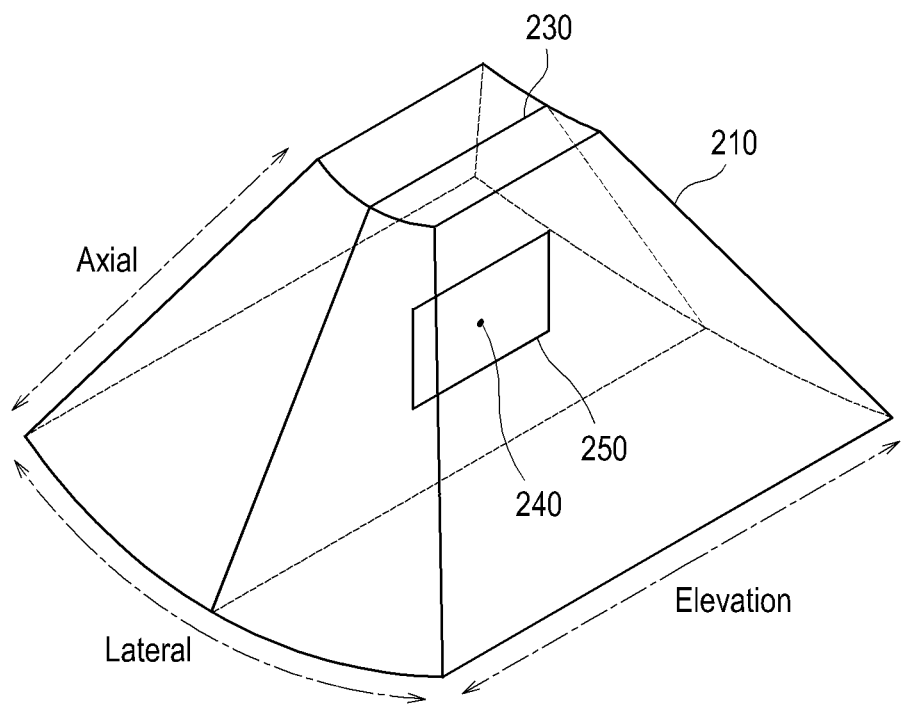
FIG. 6 is a schematic diagram showing an example of a reference slice, a reference point and a window set on the volume data.

The reference slice setting section 122 may set a reference slice 230 on the volume data 210 based on input information provided from a user input unit 130, as shown in FIG. 6. FIG. 6 is a schematic diagram showing an example of a reference slice 230, a reference point 240 and a window 250, which are set on the volume data 210. In one embodiment, the reference slice 230 in FIG. 6 may be the B plane 222 as shown in FIG. 5. However, the reference slice 230 may not be limited thereto.

Referring back to FIG. 4, the reference point setting section 123 may set a reference point 240 on the reference slice 230 based on the input information provided from the user input unit 130, as shown in FIG. 6.

The window setting section 124 may be operable to set a window 250 to encompass the reference point 240 on the reference slice 230 as shown in FIG. 6. In one embodiment, the window 250 may be a rectangular window having a predetermined size. However, the window 250 may not be limited thereto.

The sagittal view setting section 125 may set a sagittal view on the volume data 210 based on the reference slice 230, the reference point 240 and the window 250. The sagittal view may be a slice for measuring a thickness of the NT of a fetus. However, the sagittal view may not be limited thereto.

In one embodiment, the sagittal view setting section 125 may be operable to detect brightness values of pixels within the window 250 set on the reference slice 230. The sagittal view setting section 125 may be further operable to calculate a reference value based on the brightness values. The reference value may be a mean value of the brightness values or a sum value of the brightness values. However, the reference value may not be limited thereto. The sagittal view setting section 125 may further move the reference slice 230, the reference point 240 and the window 250 to the lateral direction by predetermined intervals within the volume data 210 to thereby calculate the reference values. Positions of the moved reference slice 230 and the calculated reference values may be stored in a storage unit 140. The sagittal view setting section 125 may be further operable to compare the calculated reference values to thereby detect a maximum reference value. The sagittal view setting section 125 may also move the reference slice 230, the reference point 240 and the window 250 to a position corresponding to the maximum reference value. The sagittal view setting section 125 may further rotate the reference slice 230 and the window 250 to the axial direction by predetermined angles with respect to the reference point 240 to thereby calculate the reference values. Positions of the rotated reference slice 230 and the calculated reference values may be stored in a storage unit 140. The sagittal view setting section 125 may be further operable to compare the calculated reference values to thereby detect a maximum reference value. The sagittal view setting section 125 may be further operable to rotate the reference slice 230 and the window 250 to a position corresponding to the maximum reference value. The sagittal view setting section 125 may rotate the reference slice 230 and the window 250 to the elevation direction by predetermined angles with respect to the reference point 240 to thereby calculate the reference values. The sagittal view setting section 125 may be further operable to compare the calculated reference values to thereby detect a maximum reference value. The sagittal view setting section 125 may rotate the reference slice 230 and the window 250 to a position corresponding to the maximum reference value. Thus, the sagittal view setting section 125 may set the sagittal view on the volume data 210 based on the reference slice 230. The sagittal view may include the reference point 240 and the window 250. For example, the sagittal view setting section 125 may be operable to set the reference slice 230 as the sagittal view on the volume data 210.

While the sagittal view setting section 125 may set the mean value of the brightness values or the sum value of the brightness values as the reference value in the foregoing embodiment, the sagittal view setting section 125 may further calculate a gradient magnitude and an orientation for each of the pixels within the window 250, form a histogram between the gradient magnitudes and the orientations, detect a peak in the histogram and set the detected peak as the reference value.

Also, while the sagittal view setting section 125 may move the reference slice 230 to the lateral direction and rotate the reference slice 230 to the axial direction and the elevation direction in the foregoing embodiment, the sagittal view setting section 125 may further move and rotate the reference slice 230 to arbitrary directions.

Further, while the sagittal view setting section 125 may rotate the reference slice 230 with respect to the reference point 240 in the foregoing embodiment, the sagittal view setting section 125 may further rotate the volume data 210 with respect to the reference point 240.

Figure 7:
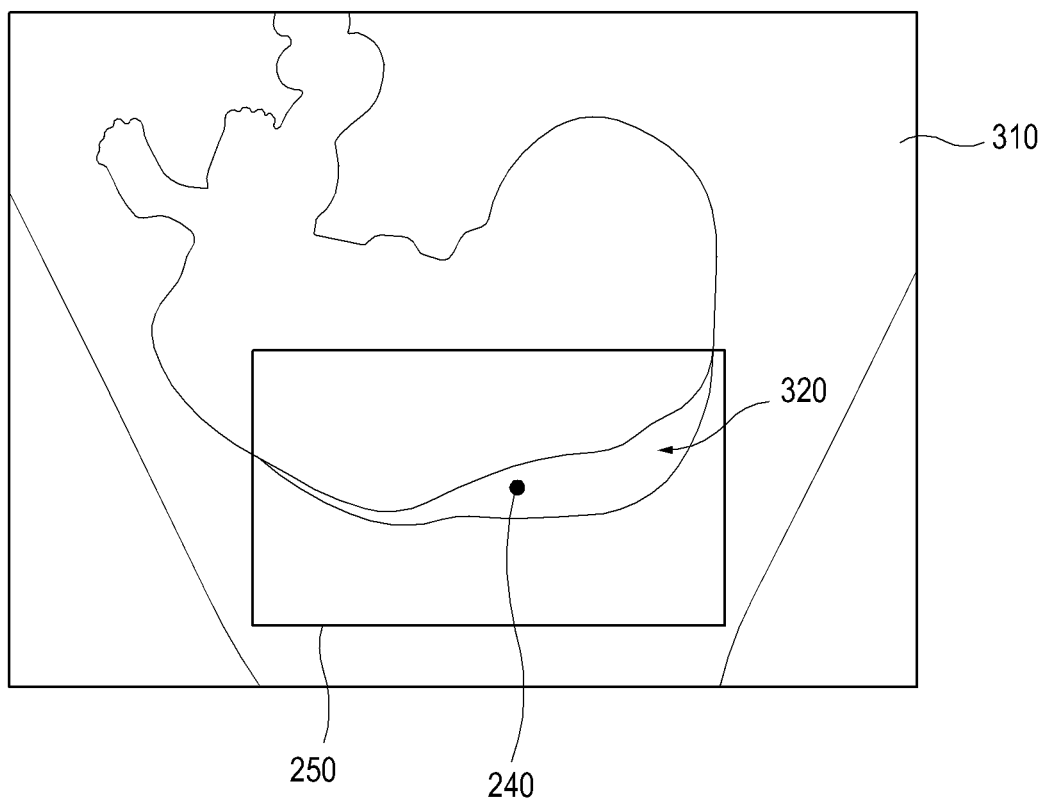
FIG. 7 is a schematic diagram showing an example of an ultrasound image, the reference point and the window.

The image forming section 126 may form a 2D (two-dimensional) ultrasound image 310 corresponding to the sagittal view based on the volume data 210 as shown in FIG. 7. FIG. 7 is a schematic diagram showing an example of the ultrasound image 310, the reference point 240 and the window 250. The 2D ultrasound image 310 may be a brightness mode image. The image forming section 126 may be further operable to render the volume data 210 to thereby form a 3D (three-dimensional) ultrasound image (not shown).

The NT thickness measuring section 127 may be configured to set the reference point 240 and the window 250 on the 2D ultrasound image 310 based on the sagittal view. The NT thickness measuring section 127 may be further configured to detect a contour of the NT 320 within the window 250. The contour may be detected by using an edge mask such as Sobel, Prewitt, Robert, Canny mask or the like. The contour may be detected based on the differences between eigenvalues using structure tensors. The NT thickness measuring section 127 may measure a thickness of the NT based on the detected contour to thereby output measurement information. The methods of measuring the thickness of the NT based on the contour are well known in the art. Thus, they have not been described in detail so as not to unnecessarily obscure the present invention.

Referring back to FIG. 1, the ultrasound system 100 may further include the user input unit 130. The user input unit 130 may be operable to receive input information of a user. In one embodiment, the input information may include first input information for setting the reference slice on the volume data and second input information for setting the reference point on the NT of the reference slice. The user input unit 130 may include a control panel, a mouse, a keyboard or the like. However, the user input unit 130 may not be limited thereto.

The ultrasound system 100 may further include the storage unit 140. The storage unit 140 may store the positions of the reference slice 230 and the reference values. The storage unit 140 may further store the volume data 210.

The ultrasound system may further include a display unit 150. The display unit 150 may display the 2D ultrasound image, the 3D ultrasound image and the measurement information.

In another embodiment, the present invention may provide a computer readable medium comprising computer executable instructions configured to perform following acts: a) transmitting and receiving ultrasound signals to and from a target object to thereby output ultrasound data; b) forming volume data based on the ultrasound data; c) setting a reference slice, a reference point and a window on the volume data based on input information of a user; and d) setting a sagittal view for measuring thickness of a nuchal translucency (NT) of a fetus on the volume data based on the reference slice, the reference point and the window. The computer readable medium may comprise a floppy disk, a hard disk, a memory, a compact disk, a digital video disk, etc.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
an ultrasound probe configured to transmit and receive ultrasound signals to and from a target object to thereby output ultrasound data;
a processor implemented in the ultrasound system and coupled to the ultrasound probe, the processor configured to:
form volume data based on the ultrasound data output from the ultrasound probe;
set a reference slice on the volume data based on input information of a user;
set a reference point on the reference slice based on the input information;
set a window to encompass the reference point on the reference slice;
change positions of the reference slice, the reference point, and the window by predetermined intervals in a first direction to thereby calculate first reference values for pixels within the window;
change the positions of the reference slice, the reference point, and the window to a position corresponding to a maximum first reference value;
change an angle of the reference slice and the window by predetermined angles with respect to the reference point to thereby calculate second reference values for pixels within the window;
change the angle of the reference slice and the window to an angle corresponding to a maximum second reference value with respect to the reference point; and
set a sagittal view for measuring a thickness of a nuchal translucency (NT) of a fetus on the volume data based on the reference slice positioned and angled according to the first reference values and the second reference values; and
a display device implemented in the ultrasound system, coupled to the processor, and configured to display the sagittal view including the window,
wherein the processor is configured to:
move the reference slice, the reference point, and the window to the first direction by the predetermined intervals within the volume data to thereby calculate the first reference values;
detect the maximum first reference value from the first reference values;
move the reference slice, the reference point and the window to the position corresponding to the maximum first reference value;
rotate the reference slice and the window by the predetermined angles with respect to the reference point to thereby calculate the second reference values;
detect the maximum second reference value from the second reference values;
rotate the reference slice and the window to the angle corresponding to the maximum second reference value to thereby set the sagittal view on the volume data; and
calculate a gradient magnitude and an orientation for pixels within the window, form a histogram between the gradient magnitude and the orientation, detect a peak in the histogram, and set the detected peak as the first or second reference value.

2. The ultrasound system of claim 1, further comprising a user input receiver implemented in the ultrasound system, coupled to the processing unit, and configured to receive the input information.

3. The ultrasound system of claim 1, wherein the input information comprises:
   a first input information for setting the reference slice on the volume data; and
   a second input information for setting the reference point on the reference slice.

4. The ultrasound system of claim 1, wherein the processor is configured to detect brightness values of pixels within the window, calculate a mean value of the brightness values, and set the mean value as the first or second reference value.

5. The ultrasound system of claim 1, wherein the processor is further configured to:
   form an ultrasound image corresponding to the sagittal view based on the volume data;
   detect a contour of the NT within the window at the ultrasound image; and
   measure thickness of the NT based on the detected contour.

* * * * *